United States Patent [19]

Falgoux et al.

[11] Patent Number: 4,543,430

[45] Date of Patent: Sep. 24, 1985

[54] PROCESS FOR THE PREPARATION OF ADDITION PRODUCTS OF EPOXIDES AND HYDROXYLATED COMPOUNDS

[75] Inventors: Daniel Falgoux, Aix en Provence; Danielle Simoulin, Meyreuil; Michel Pascal-Mousselard, Aix en Provence, all of France

[73] Assignee: BP Chimie Societe Anonyme, Courbevoie, France

[21] Appl. No.: 549,571

[22] Filed: Nov. 7, 1983

[30] Foreign Application Priority Data

Nov. 17, 1982 [FR] France .................................. 82 19231

[51] Int. Cl.$^4$ ............................................. C07C 41/03
[52] U.S. Cl. .................................... 568/678; 568/608; 568/618; 568/648; 568/649; 568/676; 260/501.15; 556/177; 556/119; 556/139; 556/56; 556/85

[58] Field of Search ............... 568/648, 678, 608, 618, 568/676, 649

[56] References Cited

U.S. PATENT DOCUMENTS 4,409,403 10/1983 Vaughan ............................. 568/648

FOREIGN PATENT DOCUMENTS 0013026 12/1979 European Pat. Off. .
2917085 11/1979 Fed. Rep. of Germany .

*Primary Examiner*—Bernard Helfin
*Attorney, Agent, or Firm*—Brooks Haidt Haffner & Delahunty

[57] ABSTRACT

Process for the preparation of addition products of epoxides and hydroxylated compounds, characterized by the fact that it comprises the reaction of an epoxide and a hydroxylated compound in the homogeneous liquid phase, in the presence, as catalyst, of a salt of trifluoromethanesulphonic acid.

10 Claims, No Drawings

PROCESS FOR THE PREPARATION OF ADDITION PRODUCTS OF EPOXIDES AND HYDROXYLATED COMPOUNDS

The present invention relates to a process for the preparation of addition products of epoxides and hydroxylated compounds by catalytic reaction in a homogeneous liquid phase.

It is already known that one can carry out addition reactions of epoxides and hydroxylated compounds in the presence of various catalysts. It is known that from this reaction one obtains a mixture of addition products of one, two or more molecules of oxide per molecule of hydroxylated compound. The product preferably sought being generally an addition product comprising a single unit derived from epoxide per molecule, the selectivity of the addition reaction in the presence of a catalyst is defined as being the ratio by weight of the quantity of addition product obtained of one molecule of epoxide per molecule of hydroxylated compound to the quantity of addition product of two molecules of epoxide per molecule of hydroxylated compound, the reaction being carried out under given operating conditions in the presence of the said catalyst.

It is already known that one can use as catalyst in this addition reaction compounds of a basic character which are soluble in the reaction medium, such as hydroxides of alkali metals, or alcoholates of these metals. These catalysts are very active, but they have the drawback of leading to reactions with a low selectivity.

It is also known that one can use catalysts of an acid nature, which are soluble in the hydroxylated compounds. In particular it is known that one can use strong acids such as sulphuric acid and the sulphonic acids or boron trifluoride. However, these catalysts, whilst leading to excellent selectivity and having a high catalytic activity, cannot be employed in the current industrial reactors, because of their corrosive action on the normal metals. Moreover, they give rise to undesired side reactions, comprising in particular in the case where ethylene oxide is used, the formation of dioxane-1-4, which is a toxic substance.

Other catalysts consisting of neutral mineral salts which are soluble in hydroxylated compounds have also already been employed, such as sodium fluoborate which leads to a high selectivity but has a comparatively weak catalytic activity. One may also mention perchlorates such as magnesium, calcium, manganese, nickel and zinc perchlorates, which are both very active and very selective. The corrosive action of these salts is slight and they would certainly be of great interest if their use on an industrial scale did not involve considerable risks of explosion due to uncontrollable decomposition phenomena, particularly when they are concentrated and subjected to a high temperature during the operation of purifying the products of the addition reaction by distillation. Phosphomolybdates and phosphomolybdic acid, which are also known as catalysts, have the advantage of being very selective, only slightly corrosive and not dangerous. Unfortunately, these catalysts have a comparatively low activity and have to be used in great concentrations in order to be effective.

Heterogeneous-phase catalytic preparation of processes of addition products of epoxides with hydroxylated compounds are also known, these processes employing catalysts which are insoluble in the reaction medium. Such processes are generally employed in installations which are very complex and very different from those used in homogeneous catalysis.

Among catalysts insoluble in hydroxylated compounds one may mention in particular the fluoroalkyl-sulphonic resins which lead to very selective reactions, particularly between ethylene oxide and water, methanol or ethanol. Unfortunately, these acid type resins have to be used at comparatively low temperatures, which are comprised in practice between 50° C. and 100° C., owing to their thermal instability. Under these conditions the reaction speed remains comparatively low.

The Applicants have now found catalysts for the preparation of addition products of an epoxide and a hydroxylated compound, these catalysts which are soluble in the reaction medium having both an extremely high level of activity and a high degree of selectivity, and what is more they do not present any risk of explosion, nor do they have a corrosive effect on the usual metals. Furthermore, these catalysts may be employed over a very wide temperature range, extending from 40° to 250° C. and for instance from 80° to 250° C.

The present invention therefore relates to a process for the preparation in the homogeneous liquid phase of addition products of an epoxide and a hydroxylated compound, which process is characterised by the fact that the reaction is carried out in the presence, as catalyst, of a salt of trifluoromethanesulphonic acid (or triflic cid) whch is soluble in the reaction medium.

According to the invention a great variety of epoxides may be used, such as for example the oxides of alkylene or epichlorhydrin. However, ethylene oxide, propylene oxide or butylene oxide are used for preference.

The hydroxylated compounds employed according to the invention may be chosen from a large number of compounds, such as alcohols, phenols and water. The alcohols employed may be primary or secondary aliphatic alcohols. It is generally preferred to use primary aliphatic alcohols, such as methanol, ethanol, propanol and n-butanol. However, very good results can also be obtained with heavier primary aliphatic alcohols comprising up to 20 carbon atoms, such as for example n-octanol or dodecanol, or with secondary aliphatic alcohols such as isopropanol or secondary butanol, or the monoethers of alkyleneglycol, since it is known that the catalysts used up to the present, particularly basic catalysts, have a comparatively low activity and low selectivity in addition reactions of epoxides on these alcohols.

According to the invention, the hydroxylated compound is generally used in a large excess by weight in relation to the epoxide, the ratio by weight of the quantity of hydroxylated compound to that of epoxide being, for example, comprised between 2 and 20.

As the salt of triflic acid (trifluoromethanesulphonate or triflate) aluminium triflate is used for preference. However, one may also employ a triflate of an alkali metal, such as for example lithium triflate, a triflate of an alkali earth metal, a triflate of a metal of Group II of the Periodic Table of Elements, such as magnesium triflate, preferably zinc triflate, a triflate of a heavy metal such as for example a cobalt, nickel, zirconium, tin triflate or a tetra-alkylammonium triflate.

The triflates used as catalysts according to the invention may be obtained easily according to preparation processes which are well-known in themselves. In particular, the triflates of the metals listed above may be prepared by the action of triflic acid on these metals or on an oxide, hydroxide or carbonate of the said metals. The majority of the triflates possess an excellent thermal stability and do not decompose except at high temperature, usually over 300° C.

The quantity of triflate employed must be sufficient to obtain the desired catalyst effect. In practice, the quantity of triflate employed is generally extremely low, very much less than the quantities of catalyst which have to be used to obtain the same reaction speeds under the same operating conditions when catalysts known hitherto are employed.

The quantity of triflate utilised may vary between 1 and 100 ppm by weight of the reaction mixture, these limits depending mainly on the nature of the reagents present, the temperature of the reaction and the residence times. In the case of the use of primary alcohols comprising 1 to 6 carbon atoms, for example, the catalytic effect is already appreciable for a catalyst concentration equal to 1 ppm in relation to the reaction mixture; however, concentrations between 2 and 50 ppm are generally preferred. In the case of reactions making use of higher alcohols comprising at least 7 carbon atoms or other hydroxylated organic compounds such as phenols and the monoethers of alkyleneglycols, the triflate concentrations in the reaction medium must generally be comprised between 10 and 100 ppm.

The reaction proceeds in the homogeneous phase, at a temprature preferably comprised between 60° C. and 250° C., and particularly between 80° C. and 150° C., under a pressure sufficient to maintain the reaction mixture in the liquid state, for example under a pressure comprised between 2.5 and 4.0 MPa. It has been found, in fact, that triflates, because of their great thermal stability, retain all their activity and selectivity up to temperatures of the order of 250° C. The reaction may also be employed in current apparatus such as, for example, steel autoclaves equipped with a stirrer or tubular reactors which can operate under pressure.

The object of the following Examples is to illustrate the present invention.

EXAMPLE 1 a. Preparation of the catalyst (aluminium triflate)

0.2 g of aluminium powder and 70 ml of water are introduced with stirring into a 250-ml glass flask. The suspension obtained is brought to 80° C., then 33.3 ml of an aqueous solution of 0.57N triflic acid is added drop by drop. This mixture is maintained with stirring at 80° C. for 2 hours, then at ambient temperature for 48 hours. The aluminium triflate obtained may then be isolated by eliminating the excess aluminium by filtration and evaporating the water at 100° C. under atmospheric pressure. In this way one recovers 3.5 g of aluminium triflate, having the formula $Al(CF_3SO_3)_3$, in the form of a white powder.

b. Preparation of the reaction mixture at ambient temperature 1,620 g of n-butanol and 18 mg of aluminium triflate prepared previously are introduced into a 5-liter steel recipient provided with a stirrer system. The mixture obtained is subjected to scavenging with nitrogen gas, in order to eliminate the air present. Next 180 g of ethylene oxide are introduced and the stirring is maintained in order to homogenise the mixture. The concentration of aluminium triflate in the reaction mixture is equal to 10 ppm.

c. Production of monobutylether of ethyleneglycol

The reaction mixture obtained above feeds a tubular reactor consisting of a stainless steel tube with an internal diameter of 4 mm and a length of 50 m by means of a dosing pump. The tubular reactor is placed in a thermal chamber maintained at 200° C. The pressure inside the reactor is maintained constant at 3 MPa. The feed of the tubular reactor is set in such a way that the mean residence time of the reaction mixture in the reactor is equal to 2 hours.

After passing into the tubular reactor, the mixture is cooled through a cooling coil; a device for automatic analysis by chromatography makes it possible to determine the composition of the final mixture.

The results are shown in Table 1. It will be seen that the conversion of ethylene oxide is complete, that is to say that the conversion rate of ethylene oxide is equal to 1.00. The quantities of monobutylethers of monoethyleneglycol, diethyleneglycol and triethyleneglycol at the end of the reaction (expressed as a percent by weight of the reaction medium) are equal to 20.3%, 2.6% and 0.1% respectively. The ratio by weight of the quantity of monobutylether of monoethyleneglycol produced to that of monobutylether of diethyleneglycol or the selectivity S of the reaction is therefore equal to 7.8, which is a comparatively high figure.

EXAMPLE 2 (COMPARATIVE)

By way of comparison a test was carried out under operating conditions identical to those of Example 1 except for the fact that instead of aluminium triflate at a concentration of 10 ppm, potassium acetate was used having the formula $CH_3COOK$, at a concentration of 50 ppm.

The results given in Table I show that, despite a catalyst concentration very much greater than that of Example 1, the conversion rate of ethylene-oxide is equal only to 0.93. In turn, the selectivity of the reaction in the presence of potassium acetate, equal to 3.8, is very inferior to that obtained with aluminium triflate.

EXAMPLES 3, 4 AND 5

In these Examples the operating conditions are identical to those of Example 1, except for the mean residence time of the reaction mixture in the tubular reactor which is 1 hour in the three Examples, and the temperature of the chamber in which the tubular reactor is placed, which is maintained at 150° C. and 120° C. respectively in Examples 4 and 5.

The results are given in Table I.

TABLE I

| Example | Catalyst Nature | Concentration (ppm) | Temperature (°C.) | Mean residence time (hr.) | (1) Conversion rate of ethylene oxide | (2) S Selectivity |
|---|---|---|---|---|---|---|
| 1 | $Al(CF_3SO_3)_3$ | 10 | 200 | 2 | 1.00 | 7.8 |
| 2 | $CH_3COOK$ | 50 | 200 | 2 | 0.93 | 3.8 |
| 3 | $Al(CF_3SO_3)_3$ | 10 | 200 | 1 | 1.00 | 7.8 |
| 4 | $Al(CF_3SO_3)_3$ | 10 | 150 | 1 | 1.00 | 6.7 |
| 5 | $Al(CF_3SO_3)_3$ | 10 | 120 | 1 | 1.00 | 6.7 |

(1) Conversion rate of ethylene oxide: ratio of the quantity of ethylene oxide which has reacted to that used.
(2) Selectivity, defined by:
$$S = \frac{\text{Weight of monobutylether of monoethyleneglycol produced}}{\text{Weight of monobutylether of diethyleneglycol produced}}$$

The analysis of these results shows clearly the extremely high catalytic activity of aluminium triflate and the high selectivity of the reaction conducted in the presence of this catalyst. It may be noted in particular, in fact, that for a catalyst concentration as low as 10 ppm, aluminium triflate renders possible a total conversion of ethylene oxide, even at a comparatively low temperature and in a relatively short residence time. It may also be seen that the selectivity of the reaction increases with the temperature.

EXAMPLES 6 TO 11 (COMPARATIVE)

By way of comparison, tests were carried out in operating conditions identical to those of Example 1, except for the fact that instead of aluminium triflate at a concentration of 10 ppm the following were used:

in Examples 6 and 7, potassium acetate ($CH_3COOK$) at concentrations of 100 and 300 ppm respectively;

in Examples 8 and 9, magnesium perchlorate with the formula $Mg(ClO_4)_2$, at concentrations of 100 and 300 ppm respectively;

in Examples 10 and 11, zinc perchlorate with the formula $Zn(ClO_4)_2$, at concentrations of 100 and 300 ppm respectively.

The results of Examples 6 to 11, and also those of Examples 1 and 2, are collected in Table II.

TABLE II

| Example | Catalysts Nature | Concentration (ppm) | Conversion rate of ethylene oxide | Content of $C_4H_9O$—$(CH_2CH_2O)_nH$ (% by weight)[1] n = 1 | n = 2 | n ≧ 3 | S Selectivity |
|---|---|---|---|---|---|---|---|
| 1 | $Al(CF_3SO_3)_3$ | 10 | 1.00 | 20.3 | 2.6 | 0.1 | 7.8 |
| 2 | $CH_3COOK$ | 50 | 0.93 | 16.3 | 4.3 | — | 3.8 |
| 6 | " | 100 | 1.00 | 16.6 | 4.6 | — | 3.6 |
| 7 | " | 300 | 1.00 | 15.3 | 4.3 | 3.5 | |
| 8 | $Mg(ClO_4)_2$ | 100 | 0.78 | 17.0 | 1.4 | — | 12.1 |
| 9 | " | 300 | 0.98 | 23.4 | 1.8 | — | 13.0 |
| 10 | $Zn(ClO_4)_2$ | 100 | 0.67 | 16.3 | 1.1 | — | 14.8 |
| 11 | " | 300 | 1.00 | 22.5 | 2.5 | 0.1 | 9.0 |

[1]Percent by weight in the reaction medium at the outlet from the reactor of the quantities of monoethyleneglycol monbutylether (n = 1), diethyleneglycol monobutylether (n = 2) and polyethyleneglycol monobutylether (n ≧ 3) produced respectively.

An examination of this Table shows that only aluminium triflate shows both a very high activity and a good selectivity at a very low concentration. In point of fact, Examples 2, 6 and 7 show by way of comparison that the activity of potassium acetate, measured by the conversion rate of the ethylene oxide, is comparatively satisfactory from catalyst concentrations of 50 ppm, but the selectivity S of the reactions is then very low. As far as the magnesium perchlorates (Examples 8 and 9) or zinc perchlorates (Example 10 and 11) are concerned, these are very selective but their activity is mediocre.

EXAMPLES 12 TO 21

In these examples one operates as in Example 1 except that:

in Examples 12 and 13 the temperature of the chamber in which the tubular reactor is placed is fixed at 150° C. and 120° C. respectively;

in Examples 14 and 15 potassium acetate is used ($CH_3COOK$) at a concentration of 50 ppm and the temperature of the chamber is fixed at 150° C. and 120° C. respectively;

in Examples 16 and 17, potassium acetate is used ($CH_3COOK$) at a concentration of 300 ppm and the temperature of the chamber is fixed at 150° C. and 120° C. respectively;

in Examples 18 and 19, magnesium perchlorate ($Mg(ClO_4)_2$) is used at a concentration of 300 ppm and the temperature of the chamber is fixed at 150° C. and 120° C. respectively;

in Examples 20 and 21, zinc perchlorate ($Zn(ClO_4)_2$) is used at a concentration of 300 ppm and the temperature of the chamber is fixed at 150° C. and 120° C. respectively.

The results of Examples 12 to 21, and also those of Examples 1, 2, 7, 9 and 11 are collected in Table III.

TABLE III

| Example | Catalyst Nature | Concentration (ppm) | Temperature (°C.) | Conversion rate of ethylene oxide | S (Selectivity) |
|---|---|---|---|---|---|
| 1 | $Al(CF_3SO_3)_3$ | 10 | 200 | 1.00 | 7.8 |
| 12 | " | 10 | 150 | 1.00 | 6.7 |
| 13 | " | 10 | 120 | 1.00 | 6.7 |
| 2 | $CH_3COOK$ | 50 | 200 | 0.93 | 3.8 |
| 14 | " | 50 | 150 | 0.65 | — |
| 15 | " | 50 | 120 | 0.37 | — |
| 7 | $CH_3COOK$ | 300 | 200 | 1.00 | 3.5 |
| 16 | " | 300 | 150 | 0.98 | 4.0 |
| 17 | " | 300 | 120 | 0.89 | — |
| 9 | $Mg(ClO_4)_2$ | 300 | 200 | 0.98 | 12.5 |
| 18 | " | 300 | 150 | 0.71 | — |
| 19 | " | 300 | 120 | 0.42 | — |
| 11 | $Zn(ClO_4)_2$ | 300 | 200 | 1.00 | 9.1 |
| 20 | " | 300 | 150 | 0.96 | 9.1 |
| 21 | " | 300 | 120 | 0.86 | — |

Analysis of this table shows clearly the advantages which the use of aluminium triflate constitutes as a catalyst for the synthesis of monoethyleneglycol monobutylether, particularly when one varies the temperature between 120° and 200° C. It is noted that aluminium triflate is the only catalyst which, although it is used at an extremely low concentration, possesses both a high selectivity and a very high activity over a wide temperature range between 120° C. and 200° C., this high activity being demonstrated by the conversion rate equal to 1.00.

EXAMPLES 22 AND 23

In these Examples the operating conditions are identical to those of Example 1, except for the fact that in the preparation of the reaction mixture, 1,620 g of n-butanol are replaced by the same weight of methanol, but the temperature of the chamber in which the tubular reactor is placed is maintained at 150° C., that in addition in Example 23, instead of aluminium triflate at a concentration of 10 ppm, potassium acetate at a concentration of 200 ppm is employed.

Table IV shows the results of the production of monoethyleneglycol monomethylether.

TABLE IV

| Example | Catalyst Nature | Concentration (ppm) | Temperature (°C.) | Conversion rate of ethylene oxide | S (Selectivity) |
| --- | --- | --- | --- | --- | --- |
| 22 | Al(CF$_3$SO$_3$)$_3$ | 10 | 150 | 1.00 | 20.0 |
| 23 | CH$_3$COOK | 200 | 150 | 1.00 | 14.3 |

Analysis of these results shows the extremely high catalytic activity of the aluminium triflate in the reaction between methanol and ethylene oxide, and also the high selectivity of the monoethyleneglycol monomethylether reaction.

EXAMPLES 24 AND 25

In these Examples the operating conditions are identical to those of Example 1, except for the fact that in the preparation of the reaction mixture 1,620 g of ethanol are used instead of 1,620 g of butanol, that the temperature of the chamber in which the tubular reactor is placed is maintained at 150° C., and that in addition in Example 25, instead of aluminium triflate at a concentration of 10 ppm, potassium acetate at a concentration of 200 ppm is employed.

Table V shows the results of the production of monoethyleneglycol monoethylether.

TABLE V

| Example | Catalyst Nature | Concentration (ppm) | Temperature (°C.) | Conversion rate of ethylene oxide | S (Selectivity) |
| --- | --- | --- | --- | --- | --- |
| 24 | Al(CF$_3$SO$_3$)$_3$ | 10 | 150 | 1.00 | 10.0 |
| 25 | CH$_3$COOK | 200 | 150 | 1.00 | 6.7 |

Analysis of these results shows the very high activity of aluminium triflate, compared with that of potassium acetate, in the reaction between ethanol and ethylene oxide. In addition, aluminium triflate is very superior to potassium acetate as regards the selectivity of the reaction for monoethyleneglycol monoethylether.

EXAMPLES 26 TO 29

In these Examples the operating conditions are identical to those of Example 1, except for the fact that in the preparation of the reaction mixture, 1,620 g of methanol are used instead of 1,620 g of butanol and 180 g of propylene oxide instead of 180 g of ethylene oxide, that in Examples 27 and 29, the temperature of the chamber in which the tubular reactor is placed is maintained at 150° C., instead of 200° C., and that in addition in Examples 28 and 29, instead of aluminium triflate at a concentration of 10 ppm, potassium acetate at a concentration of 200 ppm is employed.

Table VI shows the results of the production of monopropyleneglycol monomethylether.

TABLE VI

| Example | Catalyst Nature | Concentration (ppm) | Temperature (°C.) | Conversion rate of ethylene oxide | S (Selectivity) |
| --- | --- | --- | --- | --- | --- |
| 26 | Al(CF$_3$SO$_3$)$_3$ | 10 | 200 | 1.00 | 42.0 |
| 27 | " | 10 | 150 | 1.00 | 29.5 |
| 28 | CH$_3$COOK | 200 | 200 | 1.00 | 40.0 |
| 29 | " | 200 | 150 | 1.00 | 52.5 |

As these results show, it can be seen that aluminium triflate shows an activity which is very superior to that of potassium acetate in the reaction between methanol and propylene oxide, whilst at the same time maintaining a high selectivity at a high temperature for the production of monopropyleneglycol monomethylether. In particular, it is seen that the selectivity of the reaction in the presence of aluminium triflate grows in an unexpected manner as the temperature increases, in contrast to what is observed for reactions in the presence of potassium acetate.

EXAMPLE 30 a. Preparation of the catalyst (zinc triflate)

0.5 g of zinc powder and 70 ml of water are introduced with stirring into a 250 ml glass flask. The suspension obtained is brought to 80° C., then 22.2 ml of an aqueous solution of 0.57N triflic acid is added drop by drop. This mixture is maintained with stirring at 80° C. for 2 hours, then at ambient temperature for 48 hours. The zinc triflate obtained may then be isolated by eliminating the excess zinc by filtration and evaporating the water at 100° C. under atmospheric pressure. In this way, one recovers 3 g of zinc triflate, having the formula Zn(CF$_3$SO$_3$)$_2$, in the form of a white powder.

b. Preparation of the reaction mixture at ambient temperature

The preparation of the reaction mixture is carried out in operating conditions identical to those of Example 1, except for the fact that instead of introducing 18 mg of aluminium triflate into the recipient, 90 mg of zinc triflate prepared previously are introducing. Therefore, the concentration of zinc triflate in the reaction mixture is equal to 50 ppm.

c. Production of monobutylether of ethyleneglycol

One operates as in Example 1 by feeding the tubular reactor with the reaction mixture obtained above.

The results are shown in Table VII. It will be seen that the conversion of ethylene oxide is complete, that is to say that the conversion rate of ethylene oxide is equal to 1.00. The selectivity S of the reaction in the presence of zinc triflate, equal to 7.1, is very superior to that obtained with potassium acetate (see Example 2 comparative).

EXAMPLE 31

In this Example, the operating conditions are identical to those of Example 30, except for the fact that instead of maintaining at 200° C. the temperature of the chamber in which the tubular reactor is placed, the temperature is fixed at 150° C.

The results given in Table VII show that the conversion rate of ethylene oxide is equal to 1.00. In turn, the selectivity S of the reaction, equal to 6.6, is maintained at a high level.

TABLE VII

| EXAMPLE | CATALYST Nature | Concentration (ppm) | Temperature (°C.) | Conversion rate of ethylene-oxide | S (Selectivity) |
| --- | --- | --- | --- | --- | --- |
| 30 | Zn(CF$_3$SO$_3$)$_2$ | 50 | 200 | 1.00 | 7.1 |
| 31 | Zn(CF$_3$SO$_3$)$_2$ | 50 | 150 | 1.00 | 6.6 |

We claim:

1. Process for the preparation of addition products of expoxides and hydroxylated compounds, characterised by the fact that it comprises the reaction of an epoxide, selected from the group consisting of alkylene oxide and epichlorhydrin, and of a hydroxylated compound selected from the group consisting of an alcohol, an alkyleneglycol monoalkylether, a phenol compound and water, in a quantity such that the ratio of the hydroxylated compound/epoxide is comprised between 2 and 20 by weight, the reaction being carried out in a homogeneous liquid phase, at a temperature between 40° and 250° C., in the presence as catalyst selected from the group consisting of (a) tetra-alkylammonium triflate and (b) a trifluoromethanesulfonic acid salt of a metal selected from the group consisting of an alkali metal, a metal belonging to Group, II of the Periodic Table of Elements, aluminium, cobalt, nickel, zirconium and tin, in such a quantity that the catalyst concentration in the reaction mixture is comprised between 1 and 100 ppm by weight.

2. Process according to claim 1, characterised by the fact that the salt of the trifluoromethanesulphonic acid is aluminium trifluoromethanesulphonate.

3. Process according to claim 1, characterised by the fact that the salt of the trifluoromethanesulphonic acid is zinc trifluoromethanesulphonate.

4. Process according to claim 1, characterised by the fact that the epoxide is ethylene oxide, propylene oxide or butylene oxide.

5. Process for the preparation of addition products of epoxides and hydroxylated compounds, characterised by the fact that it comprises the reaction of an epoxide, selected from the group consisting of alkylene oxide and epichlorhydrin, and of a hydroxylated compound selected from the group consisting of an aliphatic alcohol comprising 1 to 20 carbon atoms, an alkyleneglycol monoalkylether, a phenol compound and water, in a quantity such that the ratio of the hydroxylated compound/epoxide is comprised between 2 and 20 by weight, the reaction being carried out in a homogeneous liquid phase, at a temperature between 40° and 250° C., in the presence as catalyst selected from the group consisting of (a) tetra-alkylammonium triflate and (b) a triflfuoromethanesulfonic acid salt of a metal selected from the group consisting of an alkali metal, a metal belonging to Group II of the Periodic Table of Elements, aluminium, cobalt, nickel, zirconium and tin, in such a quantity that the catalyst concentration in the reaction mixture is comprised between 1 and 100 ppm by weight.

6. Process according to claim 1, characterised by the fact that the reaction of the epoxide and the hydroxylated compound is carried out at a temperature between 60° C. and 250° C.,.

7. Process according to claim 1, characterised by the fact that the reaction of the epoxide and the hydroxylated compound is carried out at a temperature between 80° C. and 150° C.

8. Process according to claim 1, chracterised by the fact that the hydroxylated compound is methanol, ethanol or butanol.

9. Process according to claim 1, characterised by the fact that the catalyst concentration in the reaction mixture is comprised between 2 and 50 ppm by weight.

10. Process according to claim 1, characterised by the fact that the catalyst concentration in the reaction mixture is comprised between 10 and 50 ppm by weight.

* * * * *

UNITED STATES PATENT AND TRADEMARK OFFICE
CERTIFICATE OF CORRECTION

PATENT NO. : 4,543,430
DATED : September 24, 1985
INVENTOR(S) : DANIEL FALGOUX et al It is certified that error appears in the above-identified patent and that said Letters Patent is hereby corrected as shown below:

Col. 2, line 29, "cid" should read --acid--

Col. 5, Table II, Example 7, under heading ≥3, the figure should read --1.4--

Col. 5, Table II, Example 7, under heading Selectivity, figure should read --3.5--

Signed and Sealed this

Fourteenth Day of January 1986

[SEAL]

Attest:

Attesting Officer

DONALD J. QUIGG

Commissioner of Patents and Trademarks